(12) United States Patent
Hansen

(10) Patent No.: US 6,385,549 B1
(45) Date of Patent: May 7, 2002

(54) MEASUREMENT OF ACETONE IN MILK USING IR SPECTROSCOPY

(75) Inventor: Per Waaben Hansen, Lyngby (DK)

(73) Assignee: Foss Electric A/S, Hillerød (DK)

( * ) Notice: Subject to any disclaimer, the term of this patent is extended or adjusted under 35 U.S.C. 154(b) by 0 days.

(21) Appl. No.: 09/381,165

(22) PCT Filed: Mar. 20, 1998

(86) PCT No.: PCT/DK98/00110

§ 371 Date: Sep. 16, 1999

§ 102(e) Date: Sep. 16, 1999

(87) PCT Pub. No.: WO98/43070

PCT Pub. Date: Oct. 1, 1998

(30) Foreign Application Priority Data

Mar. 25, 1997 (DK) .............................................. 0342/97

(51) Int. Cl.$^7$ .............................................. G01D 18/00
(52) U.S. Cl. ............... 702/85; 250/339.09; 250/339.12; 702/28; 702/32; 436/23
(58) Field of Search ........................... 250/339, 339.09, 250/339.12, 340, 341, 343, 345; 702/32, 28, 85, FOR 115, FOR 116, FOR 117, FOR 118, FOR 156–FOR 163

(56) References Cited

U.S. PATENT DOCUMENTS

| 5,121,337 A | 6/1992 | Brown ......................... 702/28 |
| 5,252,829 A | 10/1993 | Nygaard et al. ....... 250/339.09 |
| 5,360,972 A | 11/1994 | DiFoggio et al. ...... 250/339.12 |
| 5,606,164 A | 2/1997 | Price et al. ............. 250/339.09 |
| 5,739,034 A | * 4/1998 | Arnvidarson et al. ......... 436/23 |
| 5,933,792 A | * 8/1999 | Andersen et al. ............. 702/32 |

FOREIGN PATENT DOCUMENTS

| EP | 0751388 | 1/1997 |
| WO | 9516201 | 6/1995 |
| WO | 9624832 | 8/1996 |

OTHER PUBLICATIONS

Hendrik–Jan Luinge et al, Infrared Spectrometry as a Sensor for the Early Detection of Ketosis in Cows. Publication date: 1996.

Anders H. Gustaesson, Acetone and Urea Concentration in Milk as Indicators of the Nutritional Status and the Composition of the Diet of Dairy Cows, Swedish University of Agricultural Sciences Department of Animal Nutrition and Management, 1993, pp. 6–48.

* cited by examiner

Primary Examiner—Arthur T. Grimley
Assistant Examiner—John Le
(74) Attorney, Agent, or Firm—Birch, Stewart, Kolasch & Birch, LLP

(57) ABSTRACT

A method for calibration of an IR spectrometry apparatus for providing and evaluating IR spectra in order to determine very low contents of specific components in a fluid, such as milk, and especially low contents of acetone, in a measuring range above 0, such as from 0.5 mM to 2.0 mM acetone in milk, using at least 50, such as from 50–300 known samples including at least 10 samples representing the fluid without any substantial content of the specific component for the calibration. Preferably, a good calibration for acetone shall be based on spectral information including the spectral ranges 1712–1697, 1419–1396, 1378–1353 and 1249–1226 cm$^{-1}$, or at least a substantial portion/part of said ranges. By use of the new calibration of a FT-IR-spectrometry apparatus it will be possible to determine the acetone content during the sane IR measurement process used for determining other milk parameters such as fat and protein. In a similar way other small contents of a specified component in a fluid can be determined by use of a method according to the invention.

16 Claims, 8 Drawing Sheets

MEASUREMENT OF ACETONE IN MILK USING IR SPECTROSCOPY

This application is the national phase under 35 U.S.C. §371 of PCT International Application No. PCT/DK98/00110 which has an International filing date of Mar. 20, 1998 which designated the United States of America.

TECHNICAL FIELD

The present invention relates to measurement of small amounts of a specified component in a fluid, and especially acetone and/or acetoacetate in milk.

PRIOR ART

It has for some time been desirable to be able to measure the content of acetone in milk in order to have a tool for an early detection of ketosis (a metabolic disease) in dairy cows. Methods for the determination are in fact available, but generally they are time-consuming. Besides the content of acetone there will typically be a related amount of acetoacetate. When ever in this specification the word acetone appears this means acetone and/or acetoacetate.

Recently IR spectrometry has become a preferred method for analysing milk, and accordingly it would be advantageous also to use IR spectrometry for finding the content of acetone and/or acetoacetate.

The application of IR spectral data for determination of concentrations of components in a composition is known e.g. from: WO 9516201 (Foss Electric A/S), WO 9624832 (Foss Electric A/S), U.S. Pat. No. 5,121,337, (Brown), U.S. Pat. No. 5,252,829, (Nygaard et al), U.S. Pat. No. 5,606,164 (Price et al) and EP 0751388 (Kyoto Dai-Ichi). From WO 9516201 it is known to determine added water and the related freezing point depression from IR spectral data From this document it is also known to be advantageous to increase the leverage of the known calibration samples by adding extra water to natural samples. U.S. Pat. No. 5,121,337 (Brown) discloses a method for correcting spectral data for data due to the spectral measurement process itself. Further it discloses how to estimate an unknown property and/or composition data of a sample by use of such method. U.S. Pat. No. 5,252,829 (Nygaard), owned by the applicant, discloses a method of determining urea in milk. The content of urea in milk is generally above zero but fairly low, and the successful urea determination described in the patent is based on thorough compensation for the influence by other components on the urea measurement, through use of contemporary determinations of the contributions from the other components, i.e. fat, lactose and protein. The samples used for calibration are generally samples having a considerable amount of urea, i.e. within the intended measuring range. U.S. Pat. No. 5606164 (Price et al) discloses a method and apparatus for biological fluid analyte concentration measurement using generalized distance outlier detection.

However, it has until now been considered impossible to use IR spectrometry for obtaining reliable detections of the amounts of acetone appearing in cows suffering from ketosis, cf. Hendrik-Jan Luinge, B. Lutz, P. Dobbelaar and Y. H. Schukken: "Infrared spectrometry as a sensor for the early detection of ketosis in cows", 1996. Poster presentation, S.O.N. Analytische Chemie, Lunteren, Nov. 6–7, 1995.

The present invention provides a method for calibration of an IR spectrometry apparatus for providing and evaluating IR spectra in order to determine very low contents of specific components in a fluid, such as milk, and especially low contents of acetone, such as from about 0.5 mM to about 2.5 mM acetone in milk.

The art of extracting information on the chemical content of fluid compositions from measured spectra has for some time been based on a process of "learning" or "calibrating" the IR spectrometry apparatus to enable the data processor of the apparatus to recognize certain components in a fluid. Normally, the spectra of about 15–20 known samples are measured and used together with the known values of the content in the samples to derive a calibration for the IR spectrometry apparatus. It is general knowledge to people in the art that the set of samples used for calibration must be representative for the desired range of measurements. There are several methods of calculating such calibrations, and many methods (such as PCR, MLR or PLS regression) are well known to people in the art. Hitherto the methods and apparatus avaiable have generally only been able to provide reliable measurements of contents which happen to appear in substantial amounts, i.e. that makes up a considerable fraction of the fluid, such as fat, protein and lactose in milk. In the case of acetone and/or acetoacetate the content in milk is generally zero or about zero.

SUMMARY OF THE INVENTION

The present invention provides a method for calibration of a spectrometry apparatus for providing and evaluating spectra for determination of very low concentrations of a specific component in a fluid in a specified measuring range above 0, (e.g. from 0.5 mM to 4.0 mM), by which calibration method a number of variables and corresponding coefficients (so-called B coefficients) are determined according to methods for multivariate calibration, such as PCR, MLR or PLS regression, comprising selecting and measuring a set of calibration samples including at least 30–50 known samples, e.g. from 50–300 known samples, for the calibration. According to the invention the set of calibration samples includes a number of samples representing the fluid without any substantial content of the specific component for the calibration, i.e. samples being below the specified measuring range.

The new method is based upon the use of a great number of known samples, which are measured by a spectrometry apparatus, providing a spectrum of each of the known samples (the content of the "known" samples either being known or determined by a reference method) and providing a calibration (e.g. by applying known calibration calculation methods such as PCR, MLR or PLS regression and by applying principal variables or genetic algorithms for variable selection).

The method was specifically developed for the determination of acetone in milk by use of IR spectroscopy. However, it is contemplated that the method is applicable to other types of spectroscopy for the determination of small amounts of other specific components.

Regarding the acetone and/or acetoacetate content, experience has indicated that a substantial number, e.g. about 20–30, and even better about 100 or 150, i.e. the vast majority of the calibration set (the known samples) may represent samples having none or almost no content of acetone.

The method according to the invention is advantageous because the vast majority of available samples are samples having no or almost no content of acetone. Only the few cows suffering from ketosis will provide samples which are representative for the range to be determined in order to be able to decide whether a cow suffer from ketosis or not. The most obvious solution to that problem would be to enrich a great number of natural samples with suitable amounts of acetone to provide a good calibration set.

According to the inventors experience such extended enrichment is not necessary. A few enriched samples and/or natural samples from cows suffering from ketosis will do, and the vast majority of the calibration samples can be natural samples from healthy cows, i.e. samples without any significant amount of acetone, and samples outside the desired measuring range. In this way a fairly accurate determination is possible. Further the provision of the calibration set is fairly easy, as the vast majority of samples may be natural samples.

According to a further advantageous method some of the calibration samples may be enriched samples, i.e. samples having zero or almost zero content of the specified component, whereto a number of predetermined, known amounts of the specified component being added. Accordingly a preferred set of calibration samples comprises a great number of samples having almost no content content of the specified component, and a small representative selection of samples covering the intended measuring range.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the inventon will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The method according to the invention will be explained in further details by use of examples based on measuring the content of acetone in milk. It should be emphasized that the method according to the invention in its broadest aspect also can be used for measuring other components appearing in very low concentrations in a fluid.

Figure 1:
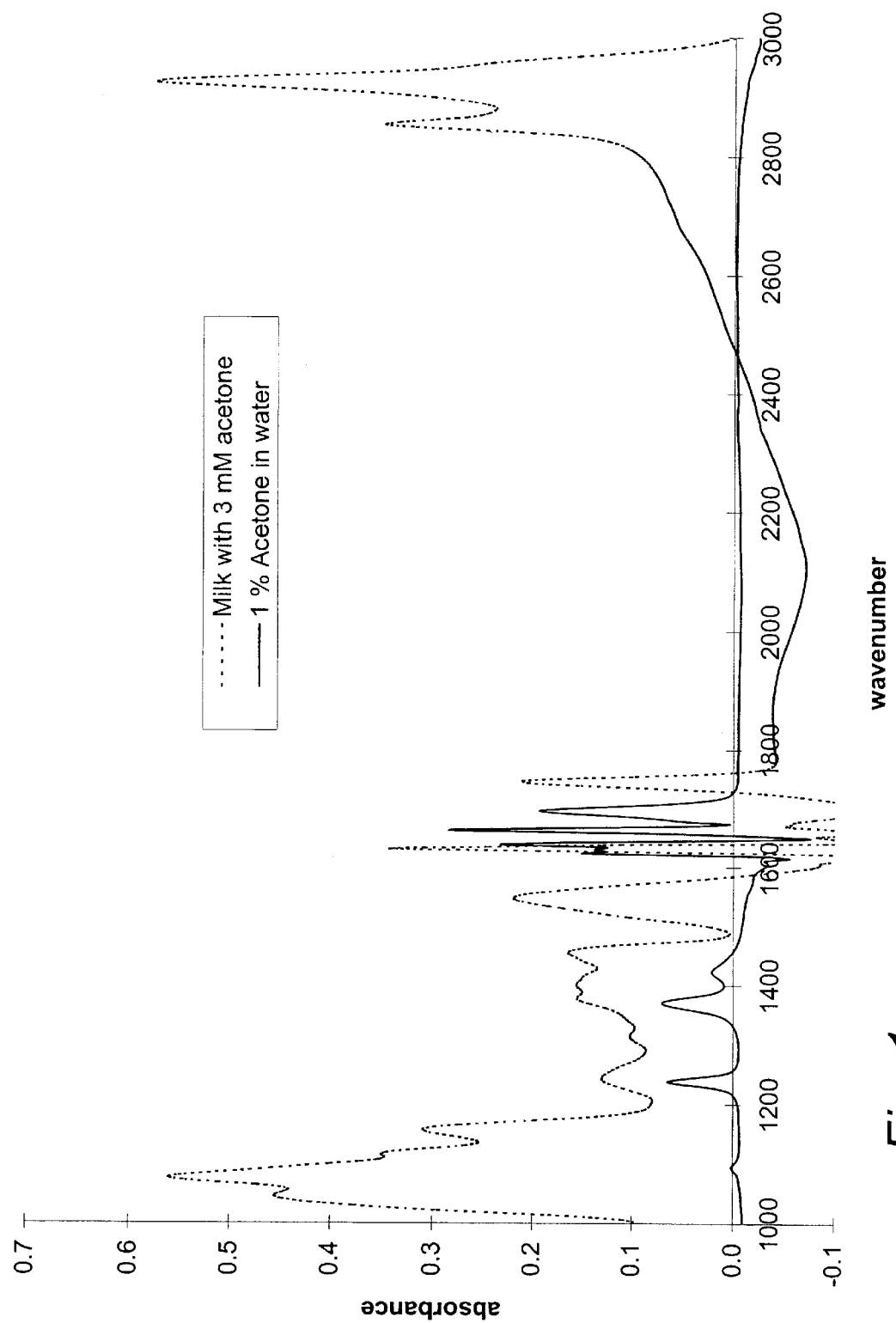
FIG. 1 shows a measured IR spectrum of a milk sample with acetone and an IR spectrum for 1% acetone in water.

Acetone has a characteristic IR spectrum that appears from FIG. 1 showing the IR spectrum of 1% acetone in water. A few seciic bands appear from the spectrum: at 1696, 1423, 1370, and 1238 $cm^{-1}$.

For the sake of good order it is mentioned that the very high signals from about 1620 to 1670 $cm^{-1}$ are caused by the water.

The concentrations of acetone appearing in milk are very low. The normal level is about 0 mM, and in case of a cow suffering from ketosis the level might reach up to about 3–4 mM.

For diagnostic purposes the following acetone limits are recommended by Anders H. Gustafsson in report 222 from the Swedish University of Agricultural Sciences, Department of Animal Nutrition and Management "Acetone and Urea Concentration in milk as indicators of the nutritional status and the composition of the diet of dairy cows":

<0.7 mM: The cow does not suffer from ketosis 0.7–1.4 mM: The cow may be ill, i.e. milk yield may be lowered >1.4 mM: The cow is ill, i.e. milk yield is reduced by 10–20%

It is mosty in the 3rd–6th week of lactation (suckling) that the cow is liable to get ketosis, due to a very high yield in this period.

From these figures it appears that milk from a normal cow (healthy cow) has an acetone content of about 0 mM. The important measuring range extends from about 0.5 mM to about 34 mM, i.e. the range that will allow an accurate diagnosis of cows suffering from ketosis. Accordingly the term "without any substantial content" used in claim 1 shall by understood as a content below the intended measuring range. In the case of acetone this means that when given the relevant measuring range extending from 0.5 to 4 mM of acetone, the calibration samples may include a number of samples having less than about 0.1 mM or 0.2 mM.

The method according to the invention comprises:

1) collecting at least 30–50 single-cow milk samples, preferably about 50–300 samples;

2a) selecting at least 5–10 and preferably about 15–30 samples from cows being in the 1st–6th wee of lactation; andlor 2b) selecting at least 5–10 and preferably about 15–30 samples for enrichment with acetone, in order to provide a representative set of samples including samples having up to about 3–4 mM of acetone, (2b may be preferred as this will surely provide the desired representative set of samples), 3) measuring all samples by a reference method (i.e. all samples to be used for the calibration);

4) measuring all samples by use of the IR spectrometry apparatus to be calibrated;

5) entering the measurement results into a data processing unit arranged to (programmed to) calculate a calibration, i.e. to make a selection of wavebands and calculate the so-called B-coefficients for the selected wavebands;

6) entering the calibration into the IR spectrometry apparatus to be calibrated.

A careful selection of single cow samples for the calibration is very important to the final result. The number of samples shall prelerably be from 50–300 known samples for the calibration. A considerable part of the samples may have zero (0) or almost zero (0) content of acetone. A second important part of the samples shall represent the specified measuring range for the content of acetone. This part may include a selection of natural samples i.e. samples from cows having ketosis. According to the inventor's experience also a selection of enriched samples can be used, as well as a mixture of natural samples and enriched samples.

At least 10–20 samples maybe enriched samples having a generally uniformly distributed variation of values covering the specified measuring range, and preferably covering more than the specified measuring range. The use of enriched samples can be an advantage in order to ensure that the calibration set includes a representative variation of the acetone content. A further advantage is that by using samples enriched by a known amount of acetone a corresponding reference measurement may be dispensed with.

In the following a number of examples Will illustrate the measurement results that can be achieved by using the method according to the invention. 171 single-cow samples were measured. 20 samples were enriched by acetone. Each of the samples were measured by a FIA (flow injection analysis) reference method and three times by use of a Foss Electric MilkoScan FT120, a FT-IR instrument using Fourier Transform-InfraRed technique, provided with a 37 μm curvet. The signal to noise ratios for the FT120 were determined at the most important wavelengths and the results are stated in table 1 below:

TABLE 1

| cm-1 | 1238 | 1365 | 1407 | 1700 |
|------|------|------|------|------|
| S/N  | 1833 | 1820 | 1267 | 508  |

The signal to noise ratios (EON) shown in table 1 were determined in the following way: Eight samples are measured three times each, with 20 seconds measuring time in a 37 μm sample cell. The transmittance is calculated on a water background. The resolution is 12 cm$^{-1}$ measured as FWHH. The RMS noise on the three determinations is calculated as the standard deviation on the transmittance at the relevant wavenumbers. The total noise is then calculated as the RMS value for the eight samples. The signal to noise value is then calculated as the average transmittance for the 24 spectra at the relevant wavenumber divided by the total noise at the same wavenumber, i.e.:

S/N=average(T(wavenumber))/sd(wavenumber, sample).

The signal to noise ratio (SIN) of the FT-IR apparatus in use will be important to the accuracy and reliability of the obtained measurements. A S/N of at least 500 and preferably at least 1000, and more preferably at least 1500 is considered to be an important parameter for the performance of the method.

The rather low S/N in the last column is due to the fact that the wavenumber, 1700, is close to the water band, which gives rise to a high signal, but little information on the content of acetone.

Figure 2:
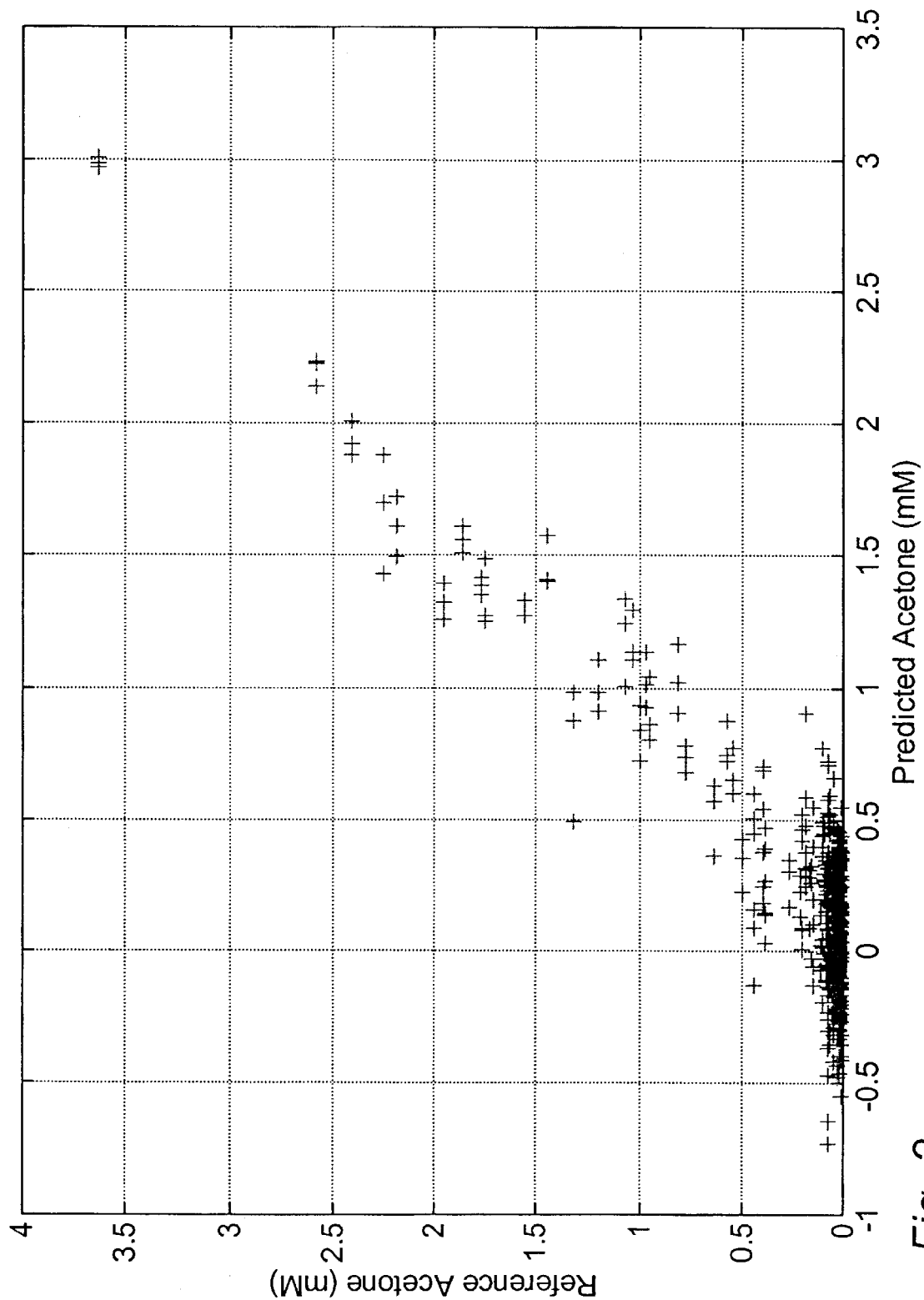
FIG. 2 shows measurement results using a full spectrum PLS model.

As a first example the full spectrum—except the water bands and a few other insignificant bands—is used. The result shown in FIG. 2 is based on a Full spectrum PLS model, using 17 factors. The validation is based on 6 cross validation segments. The cross validation is a normal validation procedure—used for testing the calibration. A fraction e.g. ⅚ of the samples are used for calibration, and the rest (the remaining segment, ⅙) is used for a validation to control whether the values obtained by use of the new calibration are comparable and preferably equal to or close to the measured reference values. The procedure is repeated 6 times—each time leaving a new segment of samples for the validation. The same type of 'cross validation' is used in all examples to follow later in this description.

FIG. 2 and all the following FIGS. 4–7 show the acetone content measured by the IR-method versus the acetone content measured by the reference method. All IR-measurements are repeated three times, so for each sample three measurement points appear as '+'. As it appears from FIG. 2 most measurement results are located in the vicinity of (0,0), in agreement with the fact that most cows are healthy, not suffering from ketosis.

Figure 3:
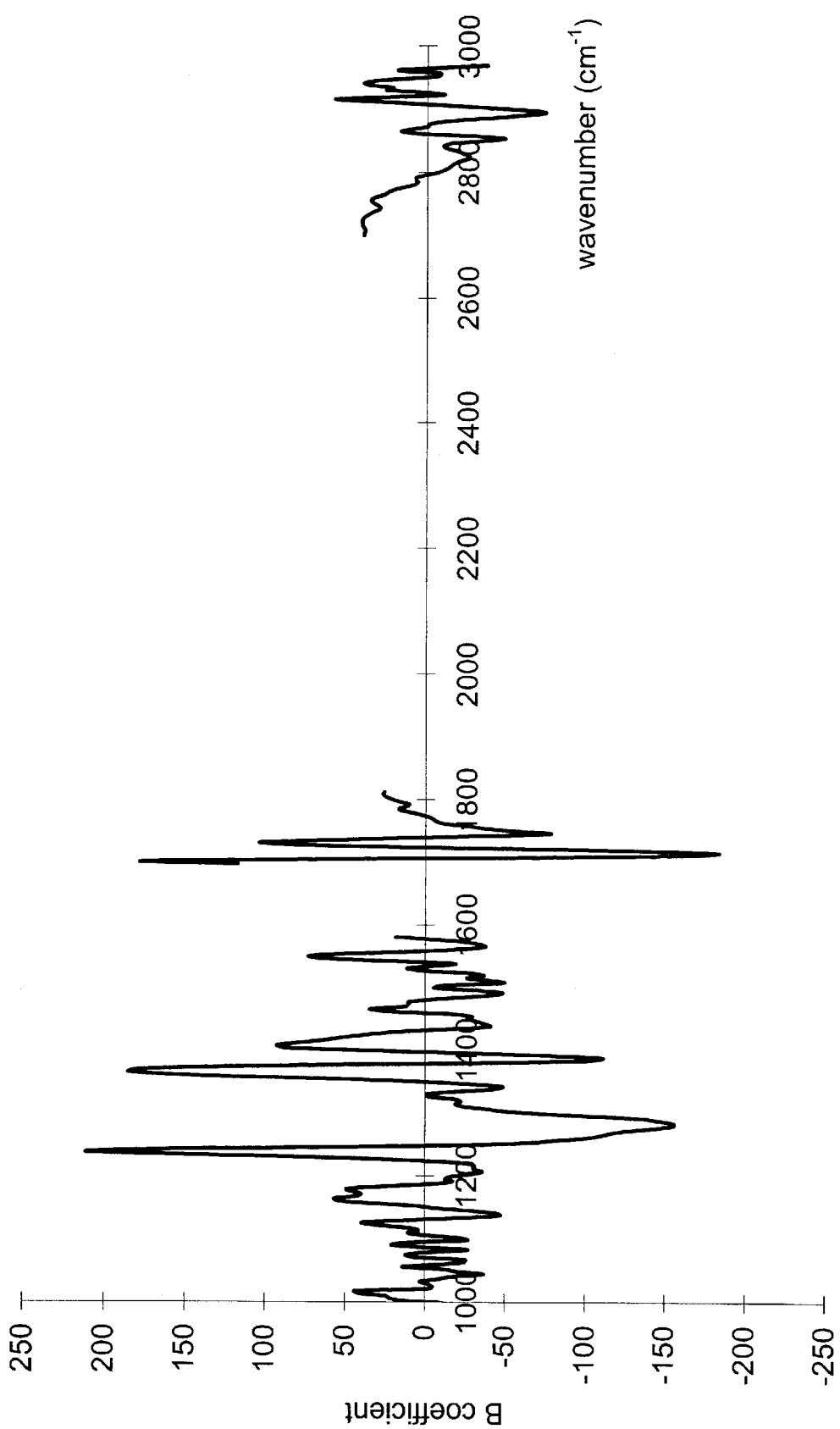
FIG. 3 shows the spectral weighting of the calibration used in FIG. 2.

The calibration—which was used for obtaining the measurements shown in FIG. 2—is shown in FIG. 3 as the spectral weighting of the calibration. The peaks appearing at 1700, 1407, 1365 and 1238 cm$^{-1}$ correspond approximately, i.e. within the resolution of the MilkoScan FT120, to the bands appearing in FIG. 1.

From FIG. 2 it appears that the few samples having a substantial content of acetone appear in close relation to a straight line from the origin, (0,0), to the point (3.0,3.6), indicating a close relation between the content measured through IR spectrometry and the content measured by the reference method. Accordingly, the acetone content in milk can be determined from IR spectrometry measurements using a calibration according to the present invention.

The performance of the method according to the invention is tested or evaluated by calculating Repeatability and Accuracy, defined as stated below:

Repeatability (REP) is stated as a mean standard deviation ($s_r$) of multiple determinations performed under identical conditions and is calculated as:

$$s_r = \sqrt{\frac{1}{q(n-1)}\sum_{j=1}^{q}\sum_{i=1}^{n}(x_{j,i} - \langle x_j \rangle)^2}$$

where q is the number of samples, n is the number of replicates, $x_{j,i}$ is the result of the i'th replicate of the j'th sample and $\langle x_j \rangle$ is the average result of the j'th sample Accuracy is stated as the Root Mean Square Error of Prediction (RMSEP) and calculated as:

$$RMSEP = \sqrt{\frac{1}{N}\sum_{i=1}^{N}(x_{i,reference} - x_{i,predicted})^2}$$

where N is the number of determinations (number of samples (q) times number of replicates (n) from above) and $x_{i,reference}$ and $x_{i,predicted}$ are the reference and predicted values corresponding to the i'th determination, respectively.

The Root Mean Square Error of Prediction (RMSEP) is found to be 0.26 mM, and the repeatability, 'REP' is 0.13 mM (i.e. $s_r$=standard deviation on multiple determinations of the same sample; in the present case all samples are measured three times on the FT-IR instrument). This result indicates that the performance is sufficient in respect to the before-mentioned diagnostic threshold values at 0.7 mM and 1.4 mM.

Further, the results shown in FIG. 2 indicate that even with RMSEP=0.26 mM it is likely that all cows measured by the method according to the invention will be classified correctly as either healthy, perhaps ill, or ill, according to the criteria mentioned before.

The following examples illustrate the reliability of the measurements in respect to different conditions for the selection of calibration samples. Table No. 2 show the data of five examples:

TABLE NO. 2

| No. of samples | No. of PLS factors | RMSEP | REP | FIG. |
|---|---|---|---|---|
| 171 | 17 | 0.26 | 0.13 | 2 |
| 100* | 18 | 0.27 | 0.13 | 4 |
| 76* | 19 | 0.28 | 0.13 | 5 |
| 76*** | 18 | 0.30 | 0.13 | 8 |
| 39** | 15 | 0.46 | 0.14 | 6 |

*The samples removed were selected randomly among all samples with an acetone content of less than 0.2 mM
**The samples removed were all samples with an acetone content of less than 0.1 mM
***The samples removed from the full dataset were selected randomly among all samples It is well known that a representative number of samples are needed for obtaining a reliable calibration model. The requested number will however depend on the type of measurement. A determination of very small amounts of acetone will require many samples. How many is investigated in the following examples referring to Table No. 2 and FIGS. 4–6 and 8.

In the first example a total of 171 samples was applied for the calibration. 17 PLS factors were found providing measurement results having RMSEP=0.26 and REP=0.13. The diagram in FIG. 2 illustrates this example. As it appears from FIG. 2 the vast majority of the samples have almost zero content of acetone. About 20 samples represent the desired measuring range from about 0.5 to about 2.5 mM.

Figure 4:
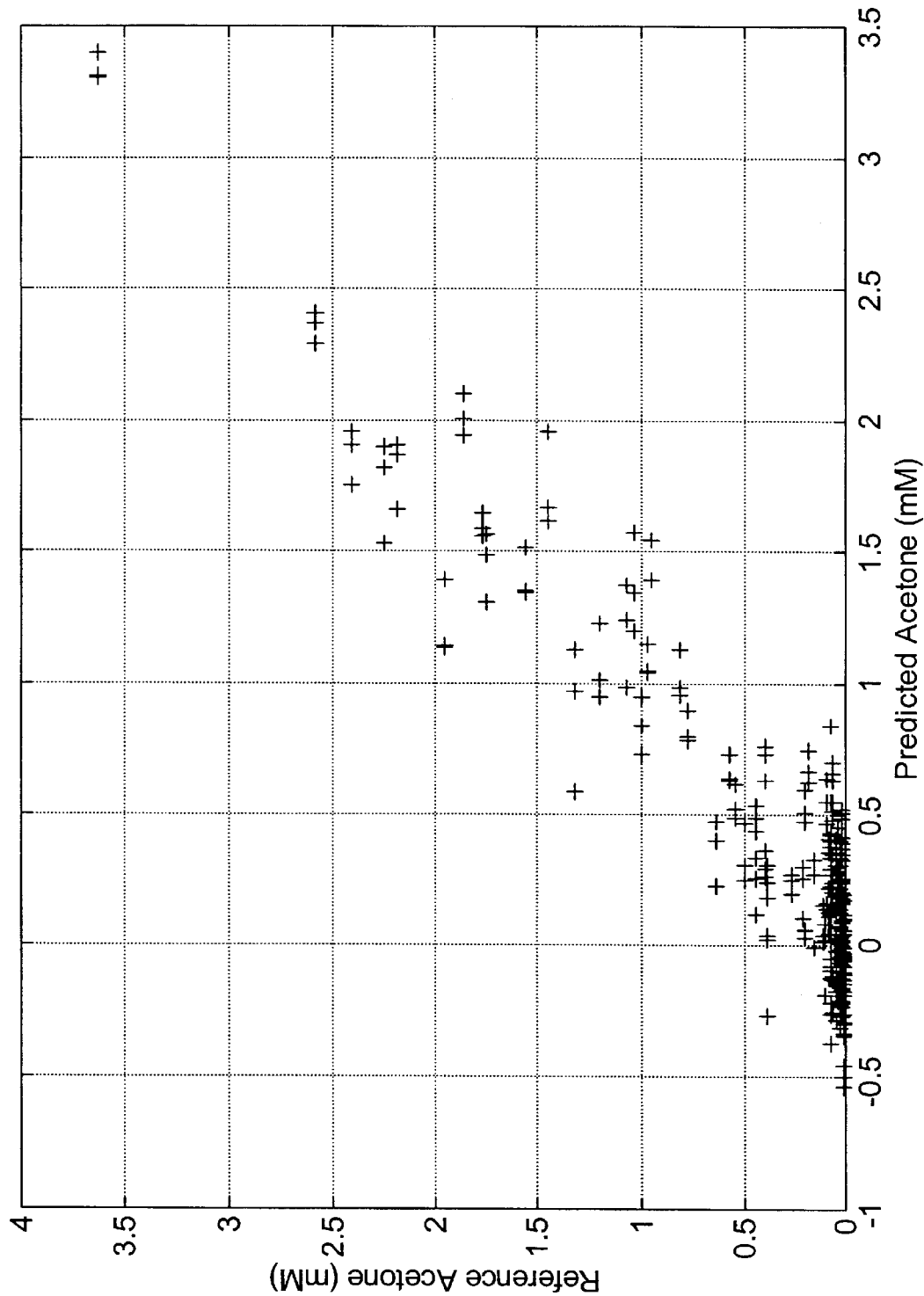
FIG. 4 shows measurement results using 100 samples and a full spectrum PLS model.

The next example (line 2 of Table 2) relates to the use of 100 samples. These were chosen by removing 71 randomly selected samples, having an acetone content of less than 0.2 mM. FIG. 4 shows a full spectrum PLS model, using the 100 remaining samples leading to 18 PLS factors and measuring results having RMSEP: 0.27 and REP: 0.13. As it appears from FIG. 4 the vast majority of the samples still have almost zero content of acetone. Again about 20 samples represent a desired measuring range from about 0.5 to about 2.5 mM.

Figure 5:
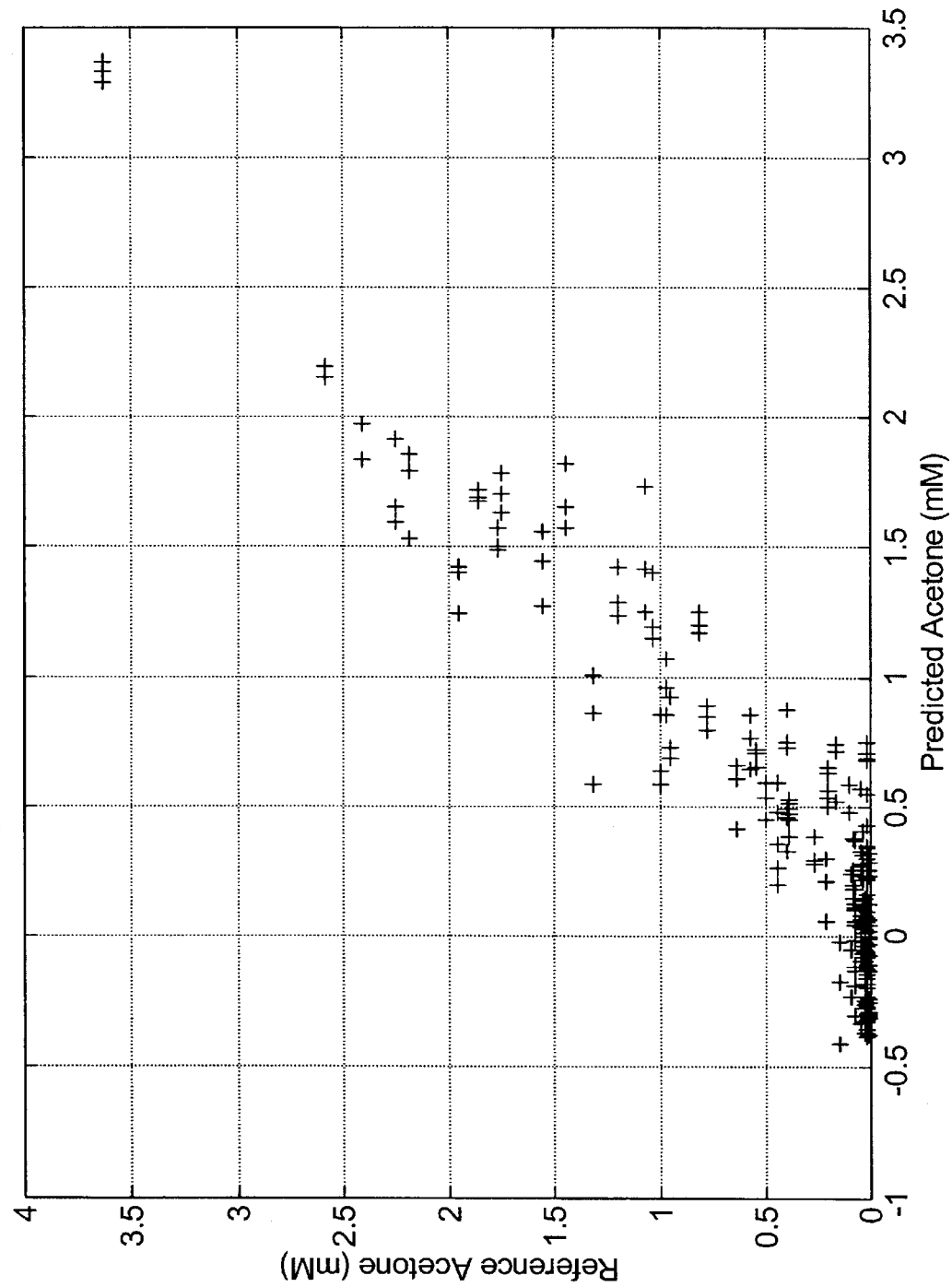
FIG. 5 shows measurement results using 76 samples and a full spectrum PLS model.

The third example (line 3 of Table 2) relates to the use of 76 samples. These were chosen by removing 95 samples randomly selected among the samples having an acetone content of less than 0.2 mM. FIG. 5 shows a full spectrum PLS model using the remaining 76 samples leading to 19 PLS factors and measuring results having RMSEP: 0.28 and REP: 0.13. As it appears from FIG. 5 a majority of the samples (about 44) have almost zero content of acetone. About 20 samples represent the desired measuring range from about 0.5 to about 25 mM.

Figure 8:
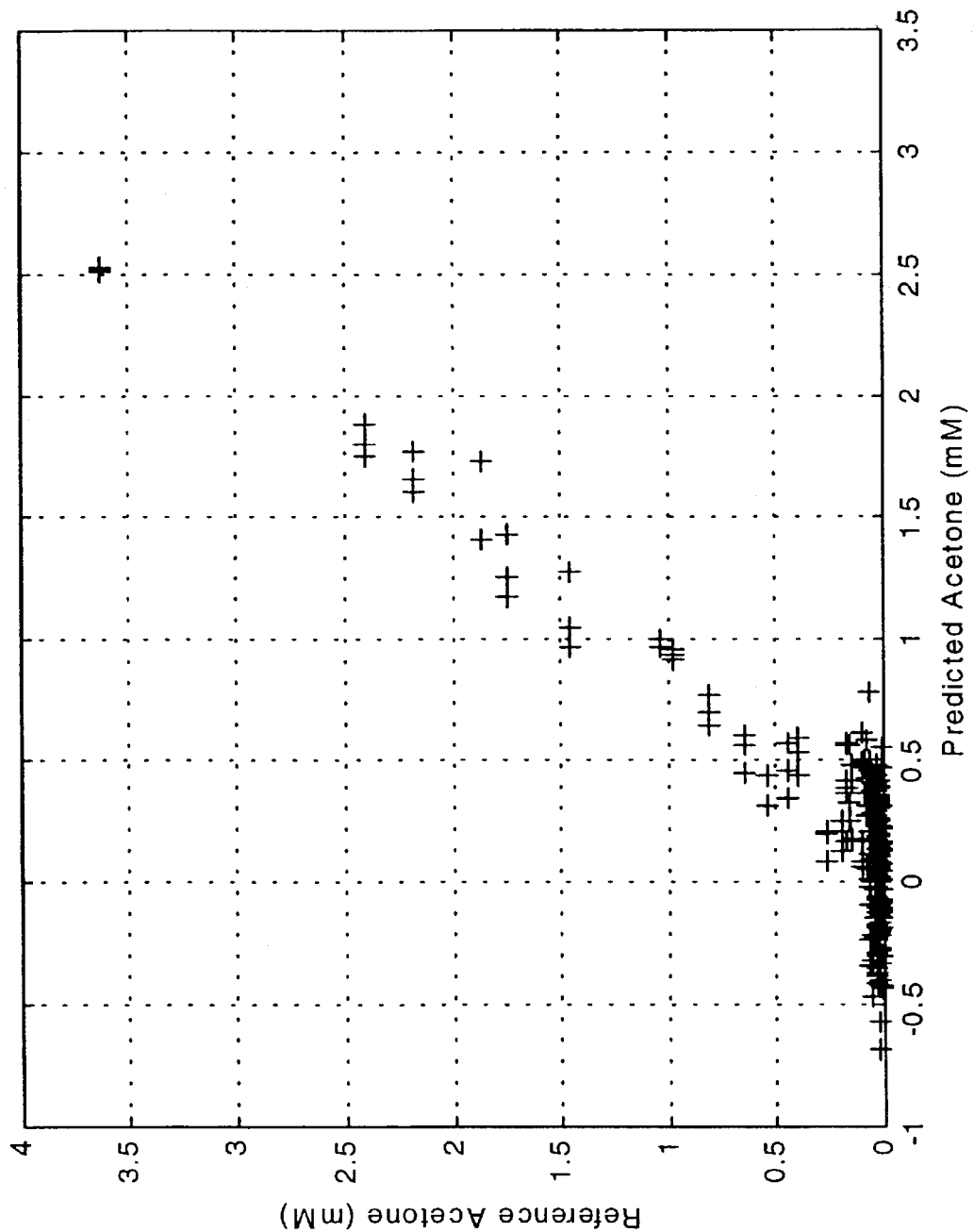
FIG. 8 shows measurement results using 76 samples and a full spectrum PLS model.

The fourth example (line 4 of Table 2) also relates to the use of 76 samples. These samples were chosen by randomly removing 95 samples from the total set of 171 samples. FIG. 8 shows a full spectrum PLS model using the remaining 76 samples leading to 18 PLS factors and measuring results having RMSEP: 0.30 and REP: 0.13. As it appears from FIG. 8 the vast majority (about 56) of the samples have almost zero content of acetone. Only about 10 samples represent the desired measuring range from about 0.5 to about 2.5 mM. Surprisingly, the accuracy seems to be satisfactory, almost as good as in example 3.

Figure 6:
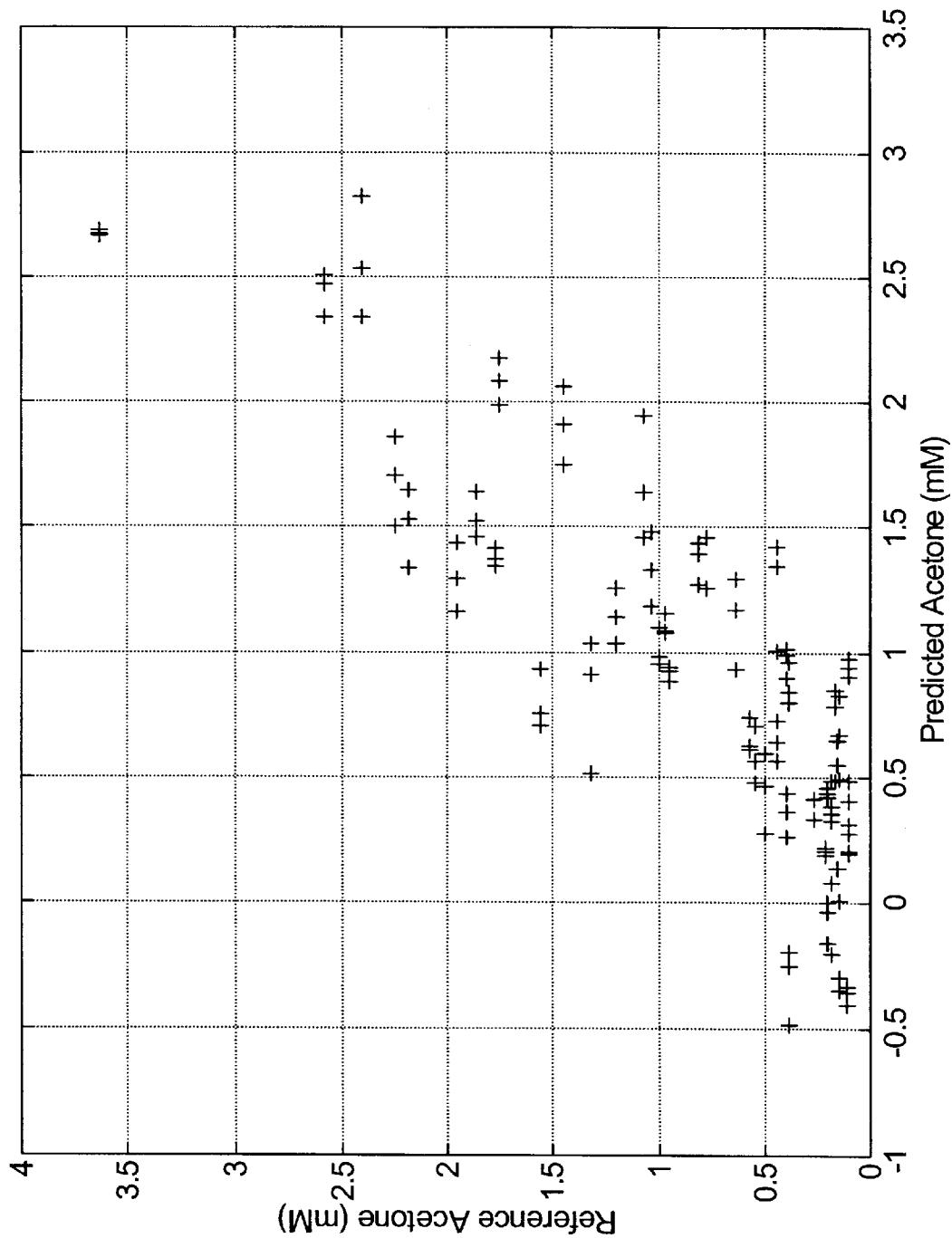
FIG. 6 shows measurement results using 39 samples and a full spectrum PLS model.

The fifth example (line 5 of Table 2) relates to the use of 39 samples. These were chosen among the 171 samples in example 1 by removing 132 samples randomly selected among samples having an acetone content of less than 0.1 mM. FIG. 6 shows a full spectrum PLS model using the remaining 39 samples leading to 15 PLS factors and measuring results having RMSEP: 0.46 and REP: 0.14. As it appears from FIG. 6 none of the samples has almost zero content of acetone. For about 18 samples the acetone content was from 0.1 to 0.5 mM. About 20 samples represent the desired measuring range from about 0.5 to about 2.5 mM. It is obvious from the FIG. 6 that the results are more scattered. The calculated RMSEP indicates that the calibration set is too poor. Accordingly, a representative set of 20 samples covering the desired measuring range is not sufficient. A great number of samples without any or almost any content of acetone clearly contribute to improve the accuracy of the determination.

From FIGS. 4–6 and 8 it appears that 100 samples or even 76 samples including about 20 samples, representing the desired measuring range, lead to a calibration being almost as good as the first one using 171 samples shown in FIG. 2 having RMSEP: 0.26 and REP: 0.13. Accordingly, the calibration set of samples may contain as few as about 10–20 representative samples and the remaining samples may have no or almost no content of acetone. Specifically, the fifth example indicates that the removal of the samples having the smallest amount of acetone results in very poor accuracy. FIG. 2 clearly shows that the vast majority of calibration samples have an acetone concentration close to 0, and below 0.1 mM.

The Acetone spectrum of FIG. 1 and the calibration shown in FIG. 3 indicate that a good calibration for acetone shall preferably be based on spectral information including the spectral ranges 1712–1697, 1419–1396, 1378–1353 and 1249–1226 cm$^{-1}$, or at least a substantial part of said ranges. Also the range 1299–1276 cm$^{-1}$ obviously add important information according to the large negative peak appearing among the calculated B-coefficients shown in FIG. 3.

Figure 7:
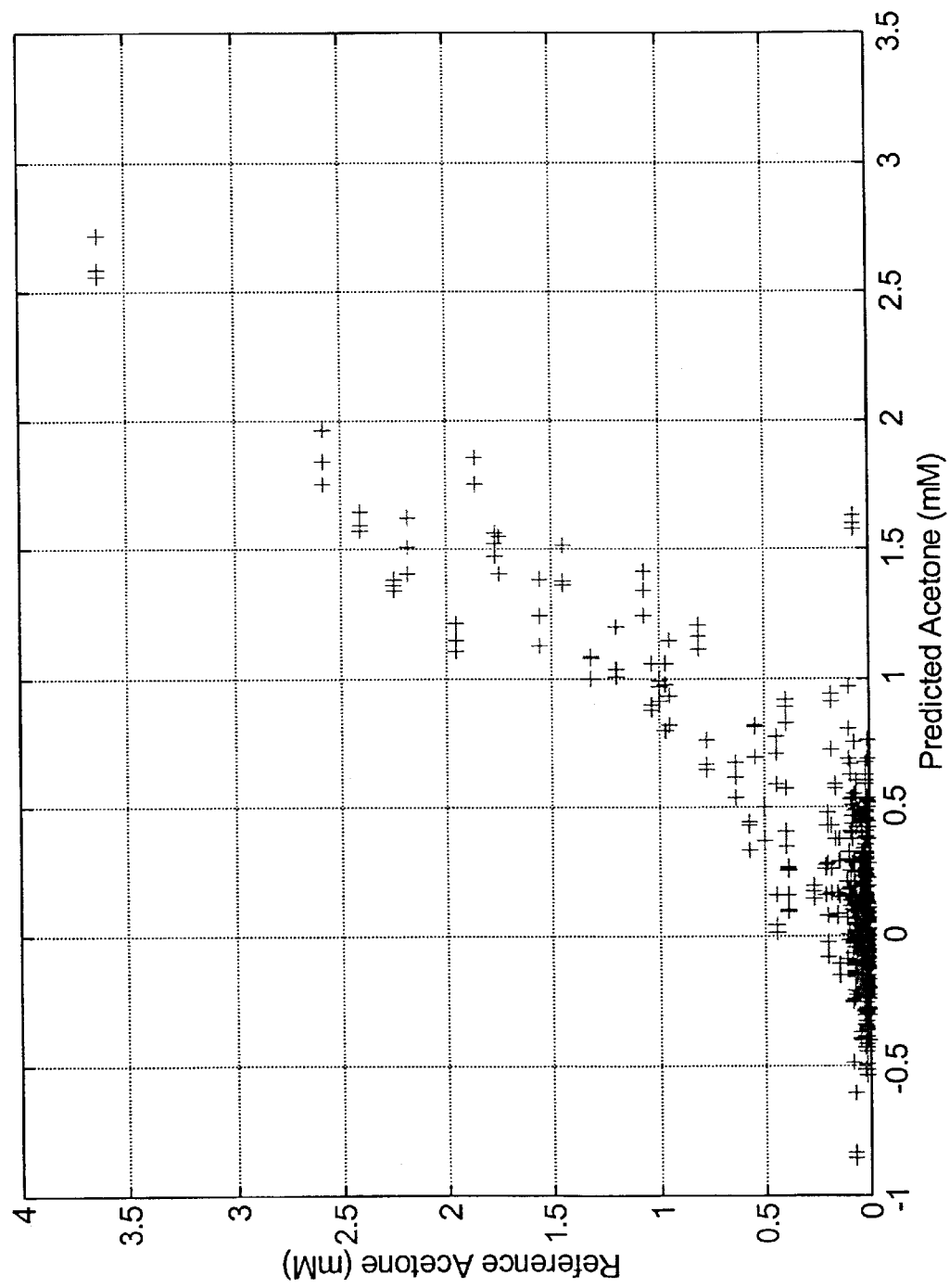
FIG. 7 shows measurement results using 171 samples, and a reduced spectrum PLS model.

FIG. 7 shows an example by which two of the said ranges were removed: The waveband 1712–1697 and 1419–1396 cm$^{-1}$, leaving the waveband ranges: 1378–1353 and 1249–1226 cm$^{-1}$. The result was a RMSEP of 0.32, and REP of 0.11; It is the experience of the inventor that at least two of the waveband ranges in question should be used in order to obtain a reliable measurement indicating whether the cow suffers from ketosis. It is preferred to use all the waveband ranges mentioned.

The method is specifically intended for measuring very small amounts of a component in a liquid. For acetone it is specifically interesting to know whether the acetone content in a milk sample is above or below 0,7 mM. According you may say that the really important measuring range is from about 0.5 to about 4 mM. Accordingly, you would expect from the knowledge of the prior art that a representative selection of known samples ought to be selected among samples in the range from about 0.5 to 4 mM. The inventor of the present method has realized the surprising fact that a great number of samples having less than 0.1 mM acetone apparently has a significant influence upon the quality of the calibration (when looking at the FIGS. 2, 4, 6, 7, 8). Here, it shall be kept in mind that the number of samples in the relevant measuring range from 0.5 mM to 4 mM are the same in the examples 1, 2, 3 and 5. Nevertheless, example 5 shows a significant decrease in accuracy compared to the examples 1, 2 and 3. The only difference is; that a great number of samples having less than 0.1 and less than 0.2 mM were included in the examples 1, 2 and 3.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for calibration of a spectrometry apparatus for providing and evaluating spectra for determination of very low concentrations of a specific component in a fluid in a measuring range above 0, by which calibration method a number of variables and corresponding coefficients are determined according to methods for multivariate calibration, the method comprising selecting and measuring a set of calibration samples including at least 30–50 known samples, for the calibration, wherein the set of calibration samples includes a majority of samples representing the fluid and having at least one of 0 and almost 0 content of the specified component for the calibration and at least 5 samples having a content of the specified component representing the measuring range for the content of the specified component.

2. A method according to claim 1, wherein the set of calibration samples includes at least 10 samples.

3. A method according to claim 1, wherein the set of calibration samples includes at least 10 samples representing the measuring range for the content of the specified component.

4. A method according to claim 3, wherein at least some of the at least 10 samples representing the measuring range for the content of the specified component are enriched samples, whereto an amount of the specified component has been added.

5. A method according to claim 4, wherein the amounts of the specified component added are predetermined known amounts.

6. A method according to claim 1, wherein at least 17 specific wavebands are used for the determination of the content of the specified component.

7. A method according to claim 1, wherein the fluid is milk and the specified component is acetone, and the spectra are IR specter, wherein at least two wavebands are used from a group of wavebands each comprising or being close to a wavenumber in the group consisting of: 1696 $cm^{-1}$, 1423 $cm^{-1}$, 1370 $cm^{-1}$, and 1238 $cm^{-1}$.

8. A method according to claim 1, wherein the fluid is milk and the specified component is acetone, wherein waveband ranges are used substantially comprising at least two waveband ranges in the group consisting of: 1712–1697 $cm^{-1}$, 1419–1396 $cm^{-1}$, 1378–1353 $cm^{-1}$, 1249–1226 $cm^{-1}$, and 1299–1276 $cm^{-1}$, and parts thereof.

9. A method according to claim 8, wherein waveband ranges are used substantially comprising at least three of the said wavebands.

10. A method according to claim 8, wherein at least spectral information is used in a spectral range in the group consisting of: 1712–1697 $cm^{-1}$, 1419–1396 $cm^{-1}$, 1378–1353 $cm^{-1}$, and 1249–1226 $cm^{-1}$, and at least a substantial portion/part of said ranges.

11. A method according to claim 1, wherein the fluid is milk and the specified component is acetone, wherein waveband ranges are used substantially comprising at least two waveband ranges in the group consisting of: 1708–1697 $cm^{-1}$, 1415–1400 $cm^{-1}$, 1373–1357 $cm^{-1}$, 1245–1230 $cm^{-1}$, and 1299–1276 $cm^{-1}$, and parts thereof.

12. A method according to claim 11, wherein waveband ranges are used substantially comprising at least three of the said wavebands.

13. A method according to claim 1, wherein any waveband is used in the group consisting of 1712–1697 $cm^{-1}$, 1419–1396 $cm^{-1}$, 1378–1353 $cm^{-1}$, 1299–1276 $cm^{-1}$, and 1249–1226 $cm^{-1}$.

14. A method for determining the content of acetone in milk, wherein an FT-IR, apparatus is used and calibrated by the method according to claim 1.

15. A method for determining the content of a specified component in a fluid, wherein an FT-IR apparatus is used and calibrated by the method according to claim 1.

16. A method for determination of very low concentrations of a specific component in a fluid, said method including a calibration of a spectrometry apparatus according to claim 1.

* * * * *

UNITED STATES PATENT AND TRADEMARK OFFICE
CERTIFICATE OF CORRECTION

PATENT NO. : 6,385,549 B1
DATED : May 7, 2002
INVENTOR(S) : Per Waaben Hansen

It is certified that error appears in the above-identified patent and that said Letters Patent is hereby corrected as shown below:

<u>Title page,</u>
ABSTRACT,
Line 15, change "sane" to -- same --.

<u>Column 1,</u>
Line 35, change "data From" to -- data. From --

<u>Column 2,</u>
Line 5, change "leaming" to -- learning --.

<u>Column 4,</u>
Line 28, change "34 mM" to -- 3 - 4 mM --.
Line 40, change "wee" to -- week --.
Line 41, change "andlor" to -- and/or --.
Line 62, change "prelerably" to -- preferably --.

<u>Column 5,</u>
Line 4, change "maybe" to -- may be --.
Line 13, change "Will" to -- will --.
Line 20, change "curvet" to -- cuvette --.
Line 29, change "(EON)" to -- (S/N) --.
Line 42, change "(SIN)" to -- (S/N) --.
Line 58, change "5/6of" to -- 5/6 of --

<u>Column 9,</u>
Line 36, change "specter" to -- spectra --.

UNITED STATES PATENT AND TRADEMARK OFFICE
CERTIFICATE OF CORRECTION

PATENT NO. : 6,385,549 B1
DATED : May 7, 2002
INVENTOR(S) : Per Waaben Hansen

It is certified that error appears in the above-identified patent and that said Letters Patent is hereby corrected as shown below:

Column 10,
Line 29, change "FT-IR" to -- FTIR --.

Signed and Sealed this

Fourteenth Day of January, 2003

JAMES E. ROGAN
*Director of the United States Patent and Trademark Office*